United States Patent
Awad et al.

(10) Patent No.: US 12,133,863 B1
(45) Date of Patent: Nov. 5, 2024

(54) GREEN SYNTHESIS OF SILVER NANOPARTICLES ENCAPSULATED IN A NANOSTRUCTURED LIPID CARRIER

(71) Applicant: KING SAUD UNIVERSITY, Riyadh (SA)

(72) Inventors: Manal Ahmed Awad, Riyadh (SA); Khalid Mustafa Ortashi, Riyadh (SA); Ali Kanakhr Aldalbahi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/583,453

(22) Filed: Feb. 21, 2024

Related U.S. Application Data

(63) Continuation of application No. 18/206,740, filed on Jun. 7, 2023.

(51) Int. Cl.
*A61K 33/38* (2006.01)
*A61K 9/127* (2006.01)
*A61K 9/51* (2006.01)
*A61P 17/02* (2006.01)
*A61P 31/04* (2006.01)
*B82Y 5/00* (2011.01)

(52) U.S. Cl.
CPC ............ *A61K 33/38* (2013.01); *A61K 9/1271* (2013.01); *A61K 9/1277* (2013.01); *A61K 9/5176* (2013.01); *A61P 17/02* (2018.01); *A61P 31/04* (2018.01); *B82Y 5/00* (2013.01)

(58) Field of Classification Search
CPC ..... A61K 9/127; A61K 9/1271; A61K 9/1277
See application file for complete search history.

(56) References Cited

U.S. PATENT DOCUMENTS

| | | | | |
|---|---|---|---|---|
| 1,764,417 | A * | 6/1930 | Satow | C01G 5/00 424/619 |
| 2004/0192908 | A1* | 9/2004 | Najib-Fruchart | A61P 17/00 549/497 |
| 2008/0312583 | A1* | 12/2008 | Oronsky | A61P 29/00 604/290 |

(Continued)

FOREIGN PATENT DOCUMENTS

| | | |
|---|---|---|
| CN | 109181844 A | 1/2019 |
| CN | 109566954 A | 4/2019 |
| CN | 109884045 A | 6/2019 |

OTHER PUBLICATIONS

Joel Toribio Espinoza et al. "Preparation and characterization of liposomes loaded with silver nanoparticles obtained by green synthesis." Brazilian Journal of Pharmaceutical Sciences, vol. 56, 2020, e18601, pp. 1-16. (Year: 2020).*

(Continued)

*Primary Examiner* — Isaac Shomer
(74) *Attorney, Agent, or Firm* — Nath, Goldberg & Meyer; Joshua B. Goldberg

(57) ABSTRACT

Green methods of synthesis of silver nanoparticles. Once the silver nanoparticles are obtained, methods of encapsulating these nanoparticles in a nanostructured lipid carrier are further contemplated. Once the encapsulated silver nanoparticles are formed, they can be used for various methods of treatment, including treating microbial infections, treating bacterial infections, and promoting wound healing.

2 Claims, 2 Drawing Sheets

(56) References Cited

U.S. PATENT DOCUMENTS

| | | | |
|---|---|---|---|
| 2015/0017258 A1* | 1/2015 | Azzazy | A01N 59/16 |
| | | | 435/5 |
| 2015/0148870 A1* | 5/2015 | Hendi | A61N 5/0625 |
| | | | 977/773 |

OTHER PUBLICATIONS

Li Xu et al. "Silver nanoparticles: Synthesis, medical applications and biosafety." Theranostics, vol. 10 Issue 20, 2020, pp. 8996-9031. (Year: 2020).*

Manal Hessien, Amel Taha, and Enshirah Da'na. "Acacia nilotica Pods' Extract Assisted-Hydrothermal Synthesis and Characterization of ZnO—CuO Nanocomposites." Materials, vol. 15, 2291, 2022, pp. 1-12, published Mar. 20, 2022. (Year: 2022).*

A. Yusuf, A. Brophy, B. Borey, and A. Casey. "Liposomal encapsulation of silver nanoparticles enhance cytotoxicity and causes induction of reactive oxygen species independent apoptosis." Journal of Applied Toxicology, 2017, pp. 1-12. (Year: 2017).*

Thomas Nesakumar Jebakumar Immanuel Edison and Mathur Gopalakrishnan Sethuraman. "Electrocatalytic Reduction of Benzyl Chloride by Green Synthesized Silver Nanoparticles Using Pod Extract of Acacia nilotica." ACS Sustainable Chemistry and Engineering, vol. 1, 2013, pp. 1326-1332. (Year: 2013).*

Burke, et al., "Hybrid Lipid-Coated Silver Nanoparticles for Drug Delivery," Portland State University, Mackiewicz Research Group, 13 pages, 2015.

Miesen, et al., "A hybrid lipid membrane coating "shape-locks" silver nanoparticles to prevent surface oxidation and silver ion dissolution," RSC Advances, Apr. 21, 2020, vol. 10, pp. 15677-15693.

Shajari, et al., "Eco-friendly curcumin-loaded nanostructured lipid carrier as an efficient antibacterial for hospital wastewater treatment", Department of Environmental science, Faculty of Natural Resources and Environment, Science and Research Branch, Islamic Azad University, Tehran, Iran, 2020.

Khezri, et al., "Efficacy of Mentha pulegium essential oil encapsulated into nanostructured lipid carriers as an in vitro antibacterial and infected wound healing agent", Department of Basic Sciences, Faculty of Veterinary Medicine, Urmia Branch, Islamic Azad University, Urmia, Iran, 2020.

Gan, et al., "Microencapsulated nanostructured lipid carriers as delivery system for rutin", Infinitus (China) Company Limited, Jiangmen, People's Republic of China; Materials Technology, 2018 vol. 33, No. 5, 357-363.

* cited by examiner

GREEN SYNTHESIS OF SILVER NANOPARTICLES ENCAPSULATED IN A NANOSTRUCTURED LIPID CARRIER

CROSS-REFERENCE TO RELATED APPLICATION

This application is a continuation of U.S. patent application Ser. No. 18/206,740, filed on Jun. 7, 2023, the entire contents of which are incorporated herein by reference.

BACKGROUND

1. Field

The disclosure of the present patent application relates to green methods of synthesis of noble metal nanoparticles, and to the encapsulation of these nanoparticles in a nanostructured lipid carrier.

2. Description of the Related Art

During the past decades, nanotechnology has attracted significant attention in the environmental applications of nanomaterials. The production of nanoparticles (NPs) from their constituent elements with a high level of control in their size and shape has been a major focus of scientific researchers to explore their application in biomedical and food industries. Silver nanoparticles (AgNPs) are one of the most popular materials among noble metal nanoparticles due to their unique chemical and physical properties and versatile applications in many fields (medicine, electronic devices, catalysis, antimicrobial agent, inks, sensors and many others).

Many methods have been used to produce AgNPs, one of the easiest and lowest-cost processes is the chemical method, which is based on a redox reaction. The right choice of the reducing agent and control in synthesis parameters guarantees the production of nanoparticles. However, alternatives to these chemical methods have been developed recently, substituting the common reducing agents with natural antioxidant compounds. These methods are called "green synthesis" because they follow the green chemistry principles.

Lipid nanocarriers are developed as an alternative to polymeric nanoparticles, liposomes and emulsions. Nanostructured lipid carriers provide ease of preparation, biocompatibility, the feasibility of scale up, non-toxicity, improved drug loading, and stability, all these properties make them a promising drug delivery system.

Thus, a synthesis method of AgNPs and methods for including them in lipid nanocarriers solving the aforementioned problems are desired.

SUMMARY

The present subject matter relates to green methods of synthesis of silver nanoparticles. Once the silver nanoparticles are obtained, methods of encapsulating these nanoparticles in a nanostructured lipid carrier are further contemplated. Once the encapsulated silver nanoparticles are formed, they can be used for various methods of treatment, including treating microbial infections, treating bacterial infections, and promoting wound healing.

In an embodiment, the present subject matter relates to a method for preparing an aqueous solution of silver nanoparticles (AgNPs), the method comprising: obtaining an *Acacia nilotica* extract; adding the *Acacia nilotica* extract to an aqueous solution of silver nitrate ($AgNO_3$) to obtain a mixture; and stirring the mixture until a color of the mixture changes from colorless to brown, thereby indicating formation of the aqueous solution of silver nanoparticles.

In another embodiment, the present subject matter relates to silver nanoparticles formed according to the present methods.

In a further embodiment, the present subject matter relates to a method of preparing silver nanoparticles encapsulated in a nanostructured lipid carrier, the method comprising: providing a preparation of a lipid in chloroform; evaporating the chloroform from the preparation; adding water to the preparation; vortexing the preparation to completely disperse the lipid in an aqueous phase; and dropwise adding the lipid in the aqueous phase to the aqueous solution of nanoparticles as prepared herein to obtain the silver nanoparticles encapsulated in the nanostructured lipid carrier.

In an additional embodiment, the present subject matter relates to a nanostructured lipid carrier comprising encapsulated silver nanoparticles prepared according to the method described herein.

In one more embodiment, the present subject matter relates to a method of treating a microbial infection in a subject comprising administering the nanostructured lipid carrier as described herein to a subject in need thereof.

In still yet another embodiment, the present subject matter relates to a method of promoting wound healing in a subject comprising administering the nanostructured lipid carrier as described herein to a subject in need thereof.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
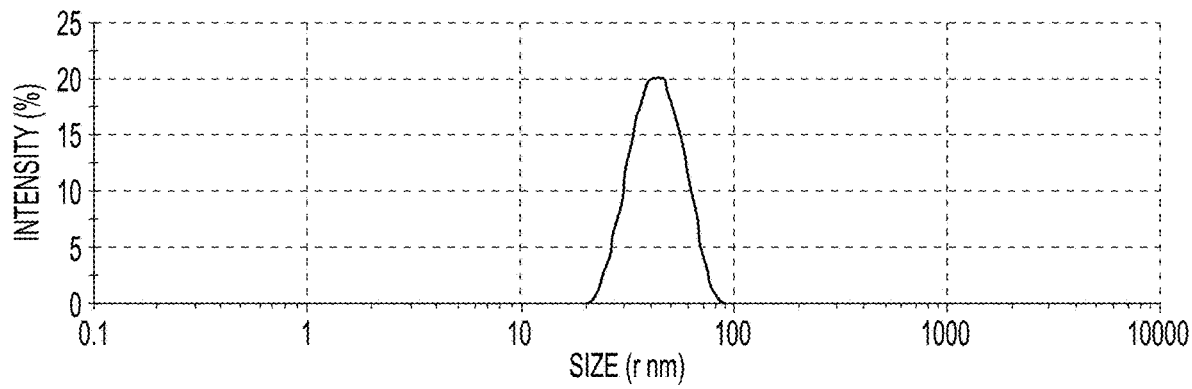
FIG. 1 is a chart showing the average size of green silver nanoparticles encapsulated into a nanostructured lipid carrier.

The following definitions are provided for the purpose of understanding the present subject matter and for construing the appended patent claims.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

The phrase "pharmaceutically acceptable," as used herein, refers to molecular entities and compositions that do not produce an allergic or similar untoward reaction when administered to a human.

The term "subject," as used herein, means a mammal, including but not limited to a human being.

As used herein, the term "providing" an agent is used to include "administering" the agent to a subject.

As used herein, a "carrier" includes any and all solvents, dispersion media, vehicles, coatings, diluents, isotonic and absorption delaying agents, buffers, carrier solutions, suspensions, colloids, excipients, and the like.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to green methods of synthesis of silver nanoparticles. Once the silver nanoparticles are obtained, methods of encapsulating these nanoparticles in a nanostructured lipid carrier are further contemplated. Once the encapsulated silver nanoparticles are formed, they can be used for various methods of treatment, including treating microbial infections, treating bacterial infections, and promoting wound healing.

In an embodiment, the present subject matter relates to a method for preparing an aqueous solution of silver nanoparticles (AgNPs), the method comprising: obtaining an *Acacia nilotica* extract; adding the *Acacia nilotica* extract to an aqueous solution of silver nitrate ($AgNO_3$) to obtain a mixture; and stirring the mixture until a color of the mixture changes from colorless to brown, thereby indicating formation of the aqueous solution of silver nanoparticles.

In one embodiment, the *Acacia nilotica* extract can be prepared by adding *Acacia nilotica* to boiling water, soaking the *Acacia nilotica* overnight, and filtering to obtain the *Acacia nilotica* extract.

In another embodiment, the aqueous solution of silver nitrate ($AgNO_3$) can be a 0.1M aqueous solution of silver nitrate. The *Acacia nilotica* extract can be added to this aqueous silver nitrate solution at a volume ratio of about 1:10 to form the mixture. In a further embodiment, the mixture can be stirred at a temperature of about 45° C., or of about 40° C. to about 50° C.

In a further embodiment, the present subject matter relates to silver nanoparticles formed according to the present methods, particularly to aqueous solutions of silver nanoparticles. In this regard, the silver nanoparticles can have a mean average diameter of about 53 nm. Further, the silver nanoparticles can be well dispersed in the aqueous solution. In addition, the silver nanoparticles can also be spherical.

In a further embodiment, the present subject matter relates to a method of preparing silver nanoparticles encapsulated in a nanostructured lipid carrier, the method comprising: providing a preparation of a lipid in chloroform; evaporating the chloroform from the preparation; adding water to the preparation; vortexing the preparation to completely disperse the lipid in an aqueous phase; and dropwise adding the lipid in the aqueous phase to the aqueous solution of nanoparticles as prepared herein to obtain the silver nanoparticles encapsulated in the nanostructured lipid carrier.

In one embodiment, the lipid used to form the nanostructured lipid carrier can be a sheep lipid.

In another embodiment, the method of preparing silver nanoparticles encapsulated in a nanostructured lipid carrier can further comprise, following the addition of the lipid in the aqueous phase to the aqueous solution of nanoparticles, stirring the aqueous solution at about 20,000 rpm at a temperature of about 45° C., or of about 40° C. to about 50°

C. In addition, the stirring of the aqueous solution can be conducted for about 15 minutes, or for about 10 to about 20 minutes.

In an additional embodiment, the present subject matter relates to a nanostructured lipid carrier comprising encapsulated silver nanoparticles prepared according to the method described herein.

In one more embodiment, the present subject matter relates to a method of treating a microbial infection in a subject comprising administering the nanostructured lipid carrier as described herein to a subject in need thereof.

In an embodiment, the microbial infection can be caused by a bacteria. In certain embodiments, the bacteria can be a Gram positive or a Gram negative bacteria. By way of non-limiting example, the bacteria can be selected from the group consisting of *Escherichia coli, Staphylococcus aureus, Streptococcus*, and any combination thereof. These treatments can be effective at various concentrations of the silver nanoparticles including, by way of non-limiting example, 15, 10, and 5 µg/ml.

In still yet another embodiment, the present subject matter relates to a method of promoting wound healing in a subject comprising administering the nanostructured lipid carrier as described herein to a subject in need thereof.

The following examples illustrate the present subject matter.

EXAMPLES

Example 1

Preparation of Silver Nanoparticle Aqueous Solutions 5 g *Acacia nilotica* was added to 15 ml of boiled deionized water, soaked all night, filtered and then the extract was kept until it was used. 5 ml of the extract was added to 50 ml of an aqueous solution of (0.1M) silver nitrate ($AgNO_3$). Afterwards, the mixture was stirred for about 10 minutes at 45° C. A color change from colorless to brown indicated the formation of the respective AgNPs nanoparticles.

Example 2

Preparation of Ag Nanoparticles encapsulated into nanostructured lipid carrier

120 µL of prepared sheep lipid (1 mg/mL) was provided in chloroform, in a glass screw-capped tube. The chloroform was evaporated under a hood. 5 mL of deionized water was added, and it was vortexed for 3 minutes to completely disperse the lipid in the aqueous phase. 3 ml of lipid in the aqueous phase was added drop wise to Ag nanoparticles solution under stirring at 20,000 rpm using a homogenizer and the temperature was maintained at 45° C. and stirring was conducted for 15 min.

Example 3

Characterization of Nanoparticles

Dynamic light scattering (DLS) techniques were used to determine the mean Z-average diameter (nm) of the synthesized AgNPs. As shown in FIG. 1, the mean average size of the resulting nanoparticles was found to be 53 nm. The polydispersity index (PDI) of the AgNP suspension was found to be 0.1, indicating that the synthesized particles showed monodisparity without an agglomeration. Further information can be found in Table 1, below.

TABLE 1

| | | Diam. (nm) | % Intensity | Width (nm) |
|---|---|---|---|---|
| Z-Average (r.nm): 53.02 | Peak 1 | 43.87 | 100.0 | 11.34 |
| Pdl: 0.198 | Peak 2 | 0.000 | 0.0 | 0.000 |
| Intercept: 0.935 | Peak 3 | 0.000 | 0.0 | 0.000 |

Example 4

Figure 2A:
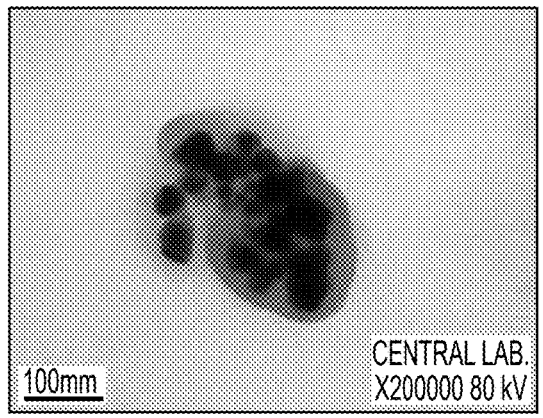
FIGS. 2A and 2B show TEM images of green silver nanoparticles encapsulated into a nanostructured lipid carrier.
Figure 2B:
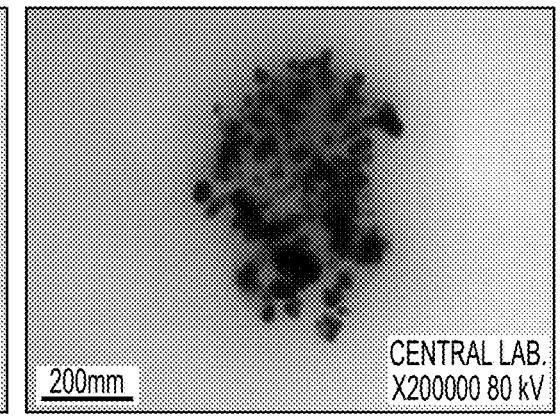

Transmission electron microscopy (TEM) was used to identify the size, shape, and morphology of the formed silver nanoparticles. It revealed that the silver nanoparticles are well dispersed and predominantly spherical in shape with a smooth surface and did not agglomerate, while some of the NPs were found to have structures of irregular shape (FIGS. 2A and 2B). TEM images revealed that all particles were spherical with a smooth surface and did not agglomerate. Finally, TEM images showed that the green synthesized silver nanoparticles capped and encapsulated into nanostructured lipid carrier.

Figure 3A:
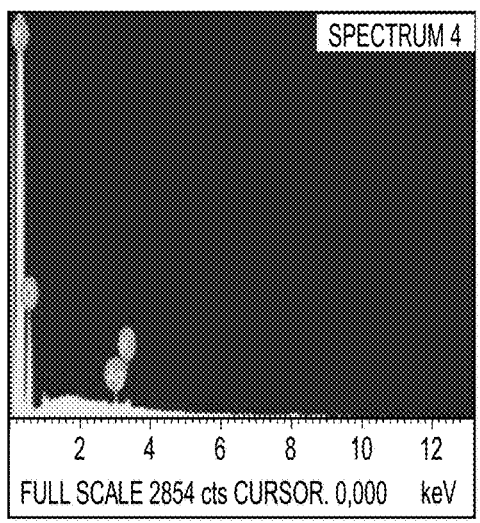
FIGS. 3A and 3B show characterizations of the synthesized silver nanoparticles using (A) energy dispersive spectroscopy spectrum; and (B) scanning electron microscopy image.
Figure 3B:
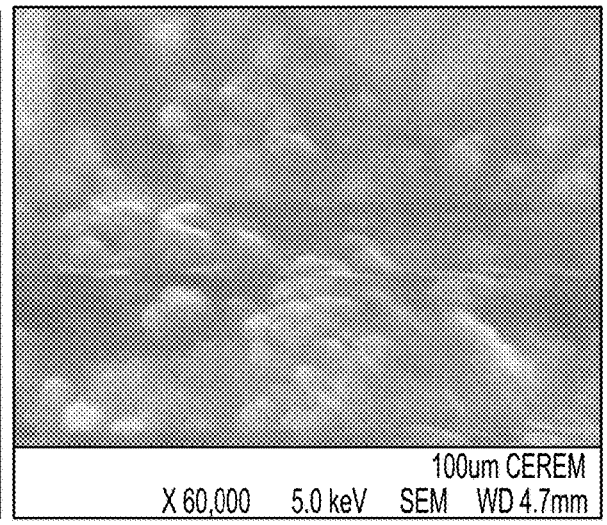

Scanning Electron Microscopy (SEM) (FIG. 3B) and Energy Dispersive spectrometer (EDS) (FIG. 3A) studies revealed the spherical capped and encapsulated synthesized nanoparticles and confirmed the existence of silver metal and the other signals of potassium and oxygen are a result of the biomolecules capped on the silver nanoparticles.

Example 5

Screening of Microbial Activity of Synthesized Ag NPs Encapsulated into Nanostructured Lipid Carrier The antimicrobial activities of the synthesized silver nanoparticles were tested by the agar disk diffusion method. The human pathogenic microorganisms used in this study included the three bacterial strains *Escherichia coli, Staphylococcus aureus*, and *Streptococcus*. The bacterial cultures were grown on blood agar at 37° C. for 18 h and the colonies were suspended in saline (0.85% NaCl) whose turbidity was adjusted to 0.5 MacFarland standards (108 CFU/mL). The bacteria were swabbed on Muller Hinton agar (MHA) plates and potato dextrose Agar (PDA) medium, respectively. The synthesized AgNPs were loaded to the sterile disk at the concentrations 15, 10 and 5 µg/ml. Then, the plates were incubated at 37° C. for 18-24 h. After incubation, the plates exhibited the formation of a clear inhibition zone around the well, which indicated the presence of antimicrobial activity. The zone of inhibition was calculated by measuring the diameter of the inhibition zone around the well.

The synthesized AgNPs exhibited promising antibacterial efficacy against pathogenic bacteria in a dose-dependent manner. In the present disclosure, the inhibition zones displayed by the synthesis of AgNPs against various pathogenic bacteria were due to the different concentrations of nanoparticles (15, 10 and 5 µg/ml). The synthesized AgNPs showed observable antibacterial activity against Gram positive bacteria such as Staph aurous and *Streptococcus*. Meanwhile, the synthesized AgNPs exhibited a large inhibition zone against the Gram negative bacteria *E. coli*. Similar results were observed and obtained with the AgNPs encapsulated into nanostructured lipid carriers, which exhibit a good antibacterial activity against both Gram-positive and Gram-negative bacteria.

Example 6

Nanoparticles Encapsulated into Nanostructured Lipid Carrier for Wound Healing (9 week, (54-110 g)) Male Wistar rats from the laboratory animal unit of King Saud University were used in this study. All animals were reared in a standard laboratory. An injury template was fashioned from a plastic 60-mL syringe by cutting a window (10×5 mm) into the back with the opposite half removed. The dorsum of each rat was carefully shaved beside the tail and laid on the injury template following anesthesia. This model would achieve approximately 10% deep partial thickness injury of total body surface area. The initial lesions were 10 mm±2 mm in the skin of rats.

Figure 4:
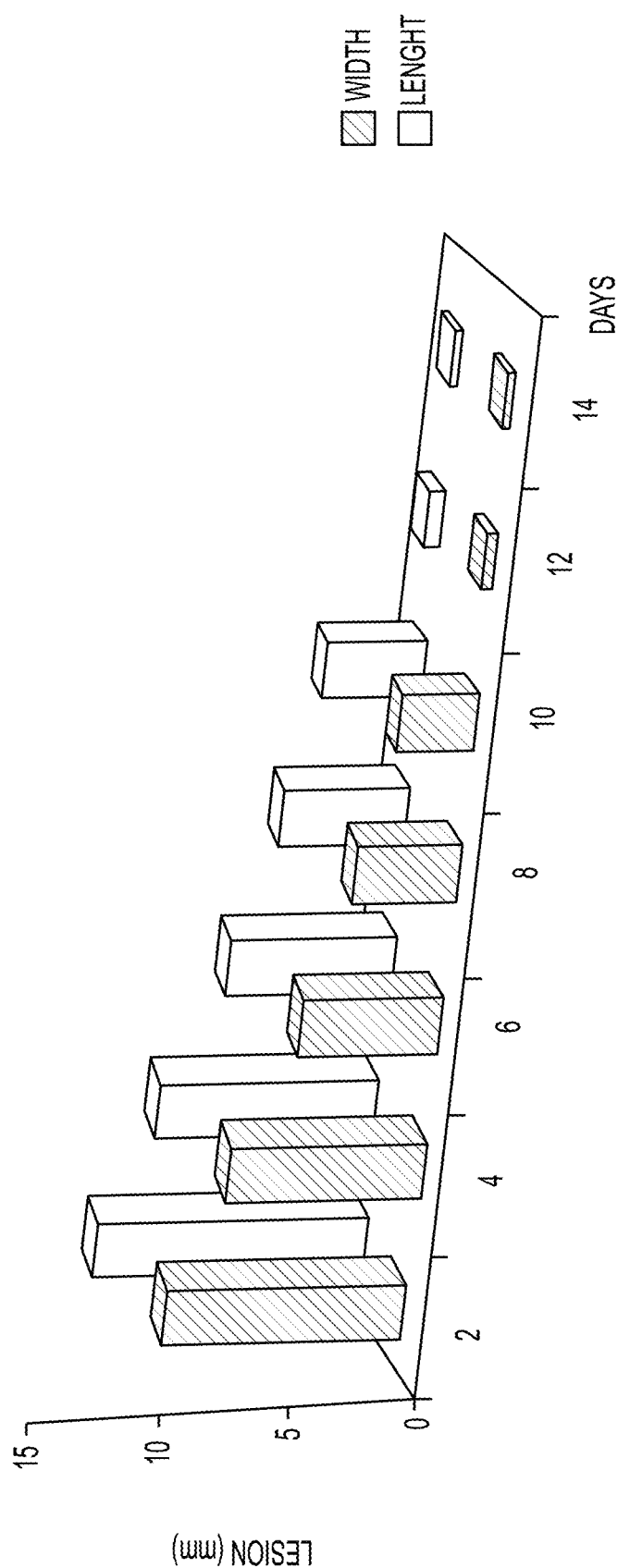
FIG. 4 is a chart of lesion size (mm) as a function of days of administration of the present silver nanoparticles.

The synthesized nanoparticles encapsulated into nanostructured lipid carrier as described herein were administered by topical application of the treatment on the wound area (daily dose (0.5 ml)). The obtained results are shown in FIG. 4.

It is to be understood that the silver nanoparticles, encapsulated silver nanoparticles, and the methods of preparing and using the same are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of preparing silver nanoparticles encapsulated in a nanostructured lipid carrier, the method consisting of:
   providing a preparation of a sheep lipid in chloroform;
   evaporating the chloroform from the preparation;
   adding water to the preparation;
   vortexing the preparation to completely disperse the sheep lipid in an aqueous phase;
   dropwise adding the lipid in the aqueous phase to an aqueous solution of nanoparticles which have been prepared by a method consisting of:
      adding *Acacia nilotica* to boiling water,
      soaking the *Acacia nilotica* overnight, and filtering to obtain the *Acacia nilotica* extract;
      adding the *Acacia nilotica* extract to an 0.1M aqueous solution of silver nitrate ($AgNO_3$) to obtain a mixture; and
      stirring the mixture at a temperature of about 45° C. until a color of the mixture changes from colorless to brown, thereby indicating formation of the aqueous solution of silver nanoparticles
   and
   stirring the aqueous solution at about 20,000 rpm at a temperature of about 45° C. to obtain the silver nanoparticles encapsulated in the nanostructured lipid carrier.

2. The method of claim 1, wherein the stirring of the aqueous solution at about 20,000 rpm at a temperature of about 45° C. is conducted for about 15 minutes.

* * * * *